(12) United States Patent
Mady et al.

(10) Patent No.: US 7,588,784 B2
(45) Date of Patent: Sep. 15, 2009

(54) USE OF ONION EXTRACTS TO PREVENT AND TREAT ACUTE AND CHRONIC CARDIAC AND VASCULAR COMPLICATIONS AND THEIR SEQUELAE, AS WELL AS TO RESOLVE HEMATOMAS

(76) Inventors: Attila Mady, 1450 S. Kihei Rd., Suite G104, Kihei, HI (US) 96753; Juliana Mady, 91 Longueuil Place, Whitby, ON (CA) L1R 3H1

( * ) Notice: Subject to any disclaimer, the term of this patent is extended or adjusted under 35 U.S.C. 154(b) by 0 days.

(21) Appl. No.: 11/868,258

(22) Filed: Oct. 5, 2007

(65) Prior Publication Data

US 2009/0092692 A1 Apr. 9, 2009

(51) Int. Cl.
*A01N 65/00* (2009.01)
*A61K 36/8962* (2006.01)
*A61F 13/00* (2006.01)
*A61K 36/00* (2006.01)

(52) U.S. Cl. .................. 424/725; 424/754; 424/449; 424/773

(58) Field of Classification Search .................. None
See application file for complete search history.

(56) References Cited

U.S. PATENT DOCUMENTS

| | | | |
|---|---|---|---|
| 4,847,276 A | | 7/1989 | Yarrington |
| 6,329,414 B1 | | 12/2001 | Thomas et al. |
| 6,555,134 B1 | | 4/2003 | Aviram et al. |
| 2004/0076689 A1 | * | 4/2004 | Hong .................. 424/728 |
| 2004/0170594 A1 | * | 9/2004 | Kadri .................. 424/74 |
| 2007/0065395 A1 | * | 3/2007 | Kim .................. 424/74 |

FOREIGN PATENT DOCUMENTS

| | | | |
|---|---|---|---|
| CN | 1650965 A | * | 8/2005 |
| GB | 235883 | | 2/1927 |
| GR | 1003636 | | 8/2001 |
| JP | 58046015 A | * | 3/1983 |
| WO | 9405307 | | 3/1994 |

OTHER PUBLICATIONS

Yamada et al., An onion variety has natural antithrombotic effect as assessed by thrombosis/thrombolysis models in rodents, Thrombosis Research, 114: 213-220, 2004.*

Walsh et al., The role of platelets in the pathogenesis of thrombosis and hemorrhage in patients with thrombocytosis, Thrombosis and Haemostasis, 38 (4): 1085-96, 1977.*

Morimitsu et al., Inhibitors of platelet aggregation generated from mixtures of Allium species and/or S-alkennyl-l-cysteine sulfoxides, J. Agric. Food Chem. 40: 368-372, 1992.*

Alan D. Michelson Platelets. 2006. Elsevier ISBN 0123693675.

Paolo Gresele Platelets in Thrombotic and Non-Thrombotic Disorders: Pathophysiology, Pharmacology and Therapeutics. 2002. Cambridge University ISBN 052180261X.

Bradford C. Berk, Judith Haendeler and Jane Sottile. Angiotensin II, atherosclerosis and aortic aneurysms. J Clin Invest. Jun. 1, 2000; 105(11): 1525-1526.

K. Schafer, S. Konstantinides (2004). PAI-1 and vasculopathy: the debate continues. Journal of thrombosis and Haemostasis 2004 (1), 13-15.

Helen Sjoland; Daniel T. Eitzman; David Gordon; Randal Westrick; Elizabeth G. Nabel; David Ginsburg. Atherosclerosis Progression in LDL Receptor-Deficient and Apolipoprotein E-Deficient Mice is Independent of Genetic Alterations in Plasminoven Activator Inhibitor-1. Atherosclerosis, Thrombosis and Vascular Biology. 2000; 20:846.

Daniel T. Eitzman, Randal J. Westrick, Zuojun Xu, Julia Tyson and David Ginsburg. Plasminogen activator inhibitor—1 deficiency protects against atherosclerosis progression in the mouse carotid artery. Blood. Dec. 15, 2000, vol. 96, No. 13, pp. 4212-4215.

Angie S. Brown; Ying Hong; Adam de Belder; Heather Beacon; Julie Beeso; Roy Sherwood; Michael Edmonds; John F. Martin; ; Jorge D. Erusalimsky. Megakaryocyte Ploidy and Platelet Changes in Human Diabetes and Atherosclerosis. Arteriosclerosis, Thrombosis, and Vascular Biology. 1997;17:802-807.)

Lilli Wiens; Gerd Lutze; Claus Luley; Sabine Westphal. Platelet count and platelet activation: Impact of a fat meal and day time. Platelets. vol. 18, Issue 2, Mar. 2007, pp. 171-173.

(Continued)

*Primary Examiner*—Michele Flood
*Assistant Examiner*—Qiuwen Mi

(57) ABSTRACT

Onions (*Allium Cepa* and its close relatives, as opposed to *Allium Sativum*) contain potent coagulation modulators, as well as platelet inhibitors. Clinical, in vivo and in vitro testing confirms that the efficacy of commonly consumed quantities of onions in terms of the efficacy of its impact on coagulation and platelet function rivals and in many respects exceeds the potency of any other modalities available today. Additionally, onion compounds have unique effects as described later in this application. The use of onion extracts is thus proposed to prevent and treat acute and chronic cardiac and vascular complications and their sequelae, to prevent and treat thrombosis, to prevent and treat embolization in the setting of thrombosis, various arrhythmias and cardiac abnormalities, as well as to resolve hematomas

11 Claims, No Drawings

OTHER PUBLICATIONS

H A Cameron, R Phillips, R M Ibbotson, and P H Carson. Platelet size in myocardial infarction. Br Med J (Clin Res Ed). Aug. 13, 1983; 287(6390): 449-451.

S. Ford. Platelet pheresis is not a useful adjunct to blood-sparing strategies in cardiac surgery. Journal of Cardiothoracic and Vascular Anesthesia. vol. 16, Issue 3, pp. 321-329, Jun. 2002.

Ronald Steriti, NMD, PhD. Thrombosis prevention, 2004.

Briggs, W. H., H. Xiao, et al. (2000). "Differential inhibition of human platelet aggregation by selected Allium thiosulfinates." J Agric Food Chem 48(11): 5731-5.

Alexopoulos K, Fatseas P, Melissari E, et al. "Design and synthesis of novel biologically active thrombin receptor non-peptide mimetics based on the pharmacophoric cluster Phe/Arg/NH2 of the Ser42-Phe-Leu-Leu-Arg46 motif sequences: platelet aggregation and relaxant activities." J Med Chem Jun. 17, 2004; 47(13):3338-52.

Alexopoulos K, Fatseas P, Melissari E, et al. Design and synthesis of thrombin receptor-derived nonpeptide mimetics utilizing a piperazine scaffold. Bioorg Med Chem Jun. 1999; 7(6):1033-41.

K. Alexopoulos, P. Fatseas, E. Melissari, D. Vlahakos, P. Roumelioti, T. Mavromoustakos, S. Mihailescu, M. Christina, P. Carbajal, D. Mascher, J. Matsoukas.(2004) Design and Synthesis of Novel Biologically Active Thrombin Receptor Non Peptide Mimetics Based on the Pharmacophoric Cluster Phe/Arg/NH2 of the Ser42-Phe-Leu-Arg46 Motif Sequence: Platelet Aggregation and Relaxant Activities. J. Med Chem. 17;47(13),3338-52.

K. Alexopoulos, D. Panagiotopoulos, T. Mavromoustakos, P. Fatseas, M.C. Paredes-Carbajal, D. Mascher, S. Mihailescu, J. Matsoukas. "Design, synthesis, and modeling of novel cyclic thrombin receptor-derived peptide analogues of the Ser42-Phe-Leu-Leu-Arg46 motif sequence with fixed conformations of pharmacophoric groups: importance of a Phe/Arg/NH2 cluster for receptor activation and implications in the design of nonpeptide thrombin receptor mimetics." J Med Chem Feb. 1, 2001; 44(3):328-39.

Efthymia Melissari, Pangiotis Fatseas . "Powerful anticoagulant and anti-blood-platelet drug for ischaemic cardiopathy A Potent Anticoagulant and Antiplatelet Substance for Ischeamic Cardiovascular Disorses." Greek Patent # 1003636, Aug. 2, 2001.

Georgios Pandalis. "Use of wild garlic for the therapy or prevention of heart rhythm disturbances." WO 94/0537 (Mar. 17, 1994).

Ali, M. and M. Thomson (1995). "Consumption of a garlic clove a day could be beneficial in preventing thrombosis." Prostaglandins Leukot Essent Fatty Acids 53(3): 211-2.

Ali, M., M. Thomson, et al. (1990). "Antithrombotic activity of garlic: its inhibition of the synthesis of thromboxane-B2 during infusion of arachidonic acid and collagen in rabbits." Prostaglandins Leukot Essent Fatty Acids 41(2): 95-9.

Beamer, N. B., B. M. Coull, et al. (1998). "Persistent inflammatory response in stroke survivors." Neurology 50(6): 1722-8.

Briggs, W. H., J. D. Folts, et al. (2001). "Administration of raw onion inhibits platelet-mediated thrombosis in dogs." J Nutr 131(10): 2619-22.

Chen, J. H., H. I. Chen, et al. (2000). "Chronic consumption of raw but not boiled Welsh onion juice inhibits rat platelet function." J Nutr 130(1): 34-7.

Dirsch, V. M., A. K. Kiemer, et al. (1998). "Effect of allicin and ajoene, two compounds of garlic, on inducible nitric oxide synthase." Atherosclerosis 139(2): 333-9.

Rahman, K. and D. Billington (2000). "Dietary supplementation with aged garlic extract inhibits ADP-induced platelet aggregation in humans." J Nutr 130(11): 2662-5.

Steiner, M. and W. Li (2001). "Aged garlic extract, a modulator of cardiovascular risk factors: a dose-finding study on the effects of AGE on platelet functions." J Nutr 131(3s): 980S-4S.

Steiner, M. and R. S. Lin (1998). "Changes in platelet function and susceptibility of lipoproteins to oxidation associated with administration of aged garlic extract." J Cardiovasc Pharmacol 31(6): 904-8.

Kleijnen et al., "Garlic, Onions and Cardiovascular risk factors. A review of the evidence from human experiments with emphasis on commercially available preparations", Br. J. Clin. Pharmac, vol. 28, pp. 535-544, (1989).

Silagy et al., "Garlic as a lipid lowering agent a meta analysis", Journal of the Royal College of Physicians of London, vol. 28, No. 1, pp. 39-45, (1994).

Warshafaky et al., "Effect of Garlic on Total Serum Cholesterol", Ann Intern Med., vol. 119, pp. 599-605, (1993).

Warshafsky et al., "Effect of Garlic on Total Serum Cholesterol", Ann. Intern. Med., vol. 119, pp. 599-605, (1993).

Kenzelmann et al., "Limitation of the Deterioration of Lipid Parameters by a Standardized Garlic-Ginkgo Combination Product", Arzneimettelforschung, vol. 43, pp. 978-981, (1993).

Auer et al., "Hypertension and hyperlipidaemia: garlic helps in mild cases", the British Journal of Clinical Practice—Supplement, vol. 69, pp. 3-6, (1990).

Vorberg e al., "Therapy with garlic: result of a placebo-controlled, double-blind study", The British Journal of Clinical Practice-Supplement, vol. 69, pp. 7-11, (1990).

Gebhardt, "Multiple Inhibitory Effects of Garlic Extracts on Cholesterol Biosynthesis in Hepatocytes", Lipids, vol. 28, No. 7, (1993).

Jain et al., "Can Garlic Reduce Levels of Serum Lipids? A Controlled Clinical Study", The American Journal of Medicine, vol. 94, pp. 632-635, (1993).

Neil et al., "Garlic powder on the treatment of moderate hyperlipidaemia: a controlled trial and meta-analysis", Journal of the Royal College Physicians of London, vol. 30, No. 4, pp. 329-334, (1996).

Endl et al., "Inhibitions of cholesterol synthesis in vitro by extracts and isolated compounds prepared from garlic and wild garlic", Atherosclerosis, vol. 94, pp. 79-95, (1992).

S. Lata Et Al., "Beneficial Effects of Allium sativum, Allium cepa and Commiphora mukul on Experimental Hyperlipidemia and Atherosclerosis- A comparative Evaluation", Journal of Postgraduate Medicinevol. 37, No. 3, pp. 132-135, 1991.

H. Heinle and E. Berz, "Effect of Dietary Garlic Supplementation in a Rat Model of Atherosclerosis", Arrneimettelforschung, vol. 44, No. 5, pp. 614-617, 1994.

T. Brosche, Et Al., "The Effect Of A Garlic Preparation On The Composition Of Plasma Lipoproteins And Erythrocyte Membranes in Geriatric Subjects", The British Journal of Clinical Practice-Supplement, vol. 69, pp. 12-19, 1990.

Jayashree Gadkari and Vijaya Joshi, "Effect of Ingestion of Raw Garlic on Serum Cholesterol Level, Clotting Time and Fibrinolytic Activity in Normal Subjects", Journal of Postgraduate Medicine, vol. 37, No. 3, pp. 128-131, 1991.

Manfred Steiner, Et Al., "A Double-Blind Crossover Study In Moderately Hypercholesterolemic Men That Compared The Effect Of Aged Garlic Extract And Placebo Administration On Blood Lipids", The American Journal of Clinical Nutrition, vol. 64, No. 6, pp. 866-870, 1996.

Rolf Gebhardt and Halgund Beck, "Differential Inhibitory Effects Of Garlic-Derived Organosulfur Compounds On Cholesterol Biosynthesis In Primary Rat Heptocyte Cultures", LIPIDS, vol. 31, No. 12, pp. 1269-1276, 1996.

Agarwal, "Therapeutic Actions of Garlic Constitutes", Medicinal Research Reviews, (1998), vol. 16, No. 1, pp. 111-124.

Lawson, "Bioactive Organosulfur Compounds of Garlic Products", Human Medicinal Agents form Plants, American Chemical Society Books, (1983), pp. 308-330, Washington.

Gebhardt, "Inhibitions of Cholesterol Biosynthesis by a Water-soluble Garlic Extract in Primary Cultures of Rat Hepatocytes", Arzneimittelforschung, (1991), vol. 41, pp. 800-804.

Stajner et al., "Antioxidant Abilities of Cultivated and Wild Species of Garlic", Phyotherapy Research, (1998), vol. 12, pp. S13, John Wiley & Sons, Ltd.

Simons et al., "On the effect of garlic on plasma lipids and lipoproteins in mild hypercholesterolaemia", Atherosclerosis, (1995), vol. 113, pp. 219-225.

* cited by examiner

USE OF ONION EXTRACTS TO PREVENT AND TREAT ACUTE AND CHRONIC CARDIAC AND VASCULAR COMPLICATIONS AND THEIR SEQUELAE, AS WELL AS TO RESOLVE HEMATOMAS

Onions (*Allium Cepa* and its close relatives, as opposed to *Allium Sativum*) contain potent coagulation modulators, as well as platelet inhibitors. Clinical, in vivo and in vitro testing confirms that the efficacy of commonly consumed quantities of onions in terms of the efficacy of its impact on coagulation and platelet function rivals and in many respects exceeds the potency of any other modalities available today. Additionally, onion compounds have unique effects as described later in this application. The use of onion extracts is thus proposed to prevent and treat acute and chronic cardiac and vascular complications and their sequelae, to prevent and treat thrombosis, to prevent and treat embolization in the setting of thrombosis, various arrhythmias and cardiac abnormalities, as well as to resolve hematomas

TECHNICAL FIELD

Disease prevention, cardiovascular disease, medicine, pharmacology.

BACKGROUND OF THE INVENTION

Cardiac and vascular disease (and, specifically, atherosclerosis) have emerged as the number one killer of modern man. It is a disease of multiple risk factors, but without a proven etiology.

Regarding the currently prevailing theory of cholesterol metabolism disarray as the most important causative factor in the genesis of cardiac and vascular disease, it is remarkable that no one has ever proposed a logical justification for the existence of increased cardiovascular risk linked to the presence of increased cholesterol. The presence of such an ontological explanation would serve to bolster the selection of cholesterol as a causative factor, rather than merely as a factor associated with increased risk of vascular disease.

It is obvious, on the other hand, why animals of many species should have inordinately high platelet counts, in excess of what might be physiologic for long mammalian lives. Even while human beings had developed the genetic capacity for long lives in prehistoric times, trauma and infection were by far the most important mechanisms of demise. Life expectancies did not pass the three decade mark in many societies until the mid $19^{th}$ century and continue to remain around this figure in several undeveloped nations today. Given these factors, it is obvious that the ability to achieve rapid and effective hemostasis would far outweigh the need for reduced intravascular events in nature. It is thus logical to assume that if the coagulation cascade can be demonstrated to be a participant in the development of vascular disease—which it is known to be—then it is likely that the survival traits of rapid hemostasis have long been in conflict with the requirements of long term patency. In other words, the "coagulation thermostat" has been selected for maximum rapidity and efficacy and this is in direct conflict with what is required for optimal blood vessel patency.

It is recognized from the experience of the primary applicant of this patent, as well as multiple other cardiovascular physicians that no patient with normally functioning platelets and chronic counts significantly below normal has ever presented with cardiovascular disease, acute or chronic. In addition, it is known that patients with Glanzmann's thrombasthenia, a genetic abnormality preventing platelet activation, are also immune to this disease. It is further known that patients undergoing cardiovascular bypass ("perfusion") and extra-corporeal membrane oxygenation for the purpose of cardiothoracic surgery experience a phenomenon known as "pump head", heretofore of unknown etiology, but logically due to activated and microaggregated platelet clusters. Finally, it is fact that the process of hemodialysis activates platelets in a manner similar to the cardiovascular bypass machines—to the extent that most patients need to be heparinized—and that patients on hemodialysis have tremendously accelerated progression of atherosclerosis.

It is known that platelets are the most unstable of all cells in the body (Ref. 1, 2). It is also known that the presence of Angiotensin II in the circulation leads to the upregulation of NF Kappa B (Nuclear Factor Kappa B) and subsequent VCAM (Vascular Cell Adhesion Molecule 1) and PAI-1 (Plasminogen Activation Inhibitor 1) production (Ref. 3), both of which enhance the progression of atherosclerosis and even gross vascular deformities such as aneurysms. Similarly, the presence and induction of activated Protein C (APC) complexes also accelerate the progression of atherosclerosis. Controversy does exist whether genetically manipulated mice with increased PAI-1 expression showed more rapid spontaneous stepwise progression of atherosclerosis with some sources adamant in denial (Ref. 4, 5) and others equally categorical in support of a factorial correlation (Ref. 6). (Note, refer to Ref. 6 also for an excellent background bibliography on current thinking regarding genesis and progression of atherosclerosis). Endothelin is felt to be another compound with a role in the genesis of atherosclerosis. Von Willebrand factor is proposed to have a role in vascular disease development and manipulation of its levels is described by U.S. Pat. No. 7,192,914. However, regardless of the individual opinions regarding causative mechanisms, there is not a single individual working on the pathogenesis of atherosclerosis today who believes that cholesterol, whether in to or a subset, is the sole or even predominant causative factor.

It is established that endovascular (i.e.: blood component) factors are more important than inherent vascular structural or chemical factors in the genesis of both micro and macrovascular disease. Specifically, contents and composition of circulating blood is more significant in the genesis of vascular pathology of all causes, whether atherosclerotic, inflammatory or other, than any structural, functional or chemical factors inherent to the vessel itself. Treatment therefore focuses on modulating the influences of these blood components, whether known or unknown.

The single most effective intervention in the prevention and treatment of vascular disease at this time remains Acetyl salicylic acid (Aspirin). Particularly for vasoocclusive disease, remarkably low doses of aspirin with remarkably low incidences of complications (less than 1% incidence of major haemorrhage) result in major outcome (death or further MI) of approximately 60%. This is even more remarkable in the light of the fact that we now know based on individual platelet function assays that up to 50% of patients treated with aspirin are non-responders, meaning genetically resistant to its acetylating effects.

It is also known that the earliest and most severe forms of atherosclerosis in the body occur at sites of maximum turbulence, such as in the aorta at the impact of a jet from a stenotic aortic valve. This mechanism of injury can only be due to intimal susceptibility or some unrecognized platelet effect, as platelets are the component of blood activated in such turbulent jets.

It is puzzling why there would be such a paucity of clinical and basic science research proceeding on the hypothesis that platelets themselves are an essential pre-requisite and final common pathway for all vascular injury. As a for instance are supplied three references (Ref. 7, 8, 9) addressing the correlation of megakaryocyte dysfunction in diseases states (specifically, diabetes), the effect of fat ingestion on platelet function and the platelet size (as a marker of platelet activation) as a positive risk for acute myocardial events (i.e.: as a marker of acute endovascular injury), respectively. Of note, however, there has not been a single study to examine whether safe reduction of platelet counts to minimum levels permissible without undue increase of major bleeding might not reduce the incidence of various vascular pathology.

Given the above clinical and basic science, as well as the fact that aspirin's effects are almost exclusively confined to the platelet component of blood, it is believed self-evident that research should concentrate on the structure and function of platelets, as well as the manipulation of said structure and function as the key to solving the riddle of the overwhelming majority of vascular diseases. A logical simple early solution to what shall indubitably prove to be an exceedingly complex mechanism and array of malfunctions is to safely manipulate the function of said platelets, as well as to regulate the anticoagulant properties of the milieu (i.e.: blood) in which they are suspended.

There is also evidence that the initial establishment of tumors is not possible without angiogenesis. In addition, is also evidence that thrombin receptors have a role in this initial angiogenesis. Platelets have a role in modulation of thrombin receptors. Reduction of platelets to safe levels would affect thrombin receptor levels.

For anyone in doubt of the veracity of the potency of platelet effect on fibroblast growth and selected cellular activity, refer to U.S. Pat. No. 5,165,938. Platelet extracts cause visible increase in fibroblast activity that can be demonstrated through gross cell culture assays. Platelets (and compounds released by platelets) have a similar inflammatory effect on white cells and multiple other blood and vascular components.

Regarding available "natural" cures, a great deal of attention has been spent on garlic and its effects. Clinical and basic research has shown little effect for garlic on its components on either cholesterol levels or coagulation. Its use has not been demonstrated to decrease cardiovascular events, or have demonstrable impact on any other medical conditions.

Curiously, though the anticoagulant properties of garlic are also known, little work has been performed to investigate these properties. All work to date has focused on the purported "anticholesterol" and "anti-oxidant" effects of garlic.

Onions are even more ignored. Used in multiple cultures worldwide as a blood thinner and "cardiac tonic", there has nevertheless been very little research regarding its composition and effects. Yet there is not only overwhelming evidence that the onion contains compounds that have a profound impact on the entirety of hemostasis (including platelet function and the coagulation cascade), but this evidence is obvious and easily demonstrable in standard platelet and coagulation assays.

Specifically, onion juice (that has not been exposed to heat and/or denaturing solvents) has been demonstrated to contain compounds that inhibit (GR1003636 addresses *Allium Sativum*, but the same compounds occur in *Allium Cepum*) initiation of the intrinsic pathway. This can be readily observed by simply instilling onion juice into a glass test tube without additives; the onion juice prevents adherence of fibrin to the glass surface, which is an activator.

Onion juice can be demonstrated through standard assays to inhibit platelet function (red onions, white and sweet, in decreasing order of potency) more effectively than any compounds known to date (red onions reduce platelet function in excess of 95%). Compounds within onions also inhibit coagulation, primarily through reducing activation through the extrinsic pathway. They also affect the later cascade components and have regulatory effects on the intrinsic pathway.

Ironically, onions also enhance certain aspects of the coagulation process. Specifically, onion juice increases the speed of clot formation (once initiated). The addition of onion juice to fresh blood in a standard warm water bath will result in more rapid completion of clotting (once clotting is initiated). CN1102186 notes that onion juice enhances platelet agglutination.

However, the most obvious and dramatic effect of onions is on thrombolysis. Topical application of sufficient amounts of onion juice to a site anywhere approximate to a hematoma (and at sufficiently frequent intervals, approximately every 6 hours) will result in the absorption of said hematoma even days after the formation of this hematoma. Even more remarkably, re-absorption shall occur at sites where there is NEVER reabsorption without surgical drainage, such as subperiosteal pretibial and olecranon hematomas. Due to the absence of blood flow in these areas, an incision and drainage are always necessary to prevent the progression to fibrosis and the development of permanent tissue deformity.

Hematoma resorption does not only occur in places where it never would under spontaneous circumstances, but is also accelerated, meaning absorption occurs more rapidly (approximately 5-7 times faster than without onion juice). Hematoma resorption is also more complete, reducing the incidence of residual hemosiderin deposition. Finally, hematoma resorption will occur long after it would on a spontaneous basis, up to a week after the initial injury. There is no other thrombolytic known that works beyond approximately 12 hours after initial clot formation.

Onion juice thus fits perfectly the Chinese concept of a "cardiac and circulatory tonic". Multiple components in onion juice work together to increase the threshold of activation both of the extrinsic and intrinsic coagulation pathways, potentiate the velocity of clotting, once initiated, reduce platelet aggregation and therefore confine the extent of clotting to conform more accurately to the site of injury and dramatically increase the extent and speed of thrombolysis. In other words, it appears on the face of the current evidence that the multiple compounds contained in cold extracted onion juice work together to not only inhibit, but to rebalance hemostasis. This indeed conforms to the concept of a tonic, meaning something that improves existing function.

In conclusion, onions are known to have profound effects on all aspects of the hemostatic process. While whole onion juice (cold-extracted) is primarily inhibitory to platelet function and coagulation (extrinsic and intrinsic), it also accelerates the speed of clot formation (i.e.: the velocity of completion of enzymatic cleavage of the various components) and also accelerates the speed and extent of thrombolysis. Overall, however, the most relevant fact remains that in spite of all these demonstrable (and dramatic) effects onions have never been noted to cause excessive bleeding.

SUMMARY OF THE INVENTION

The use of onion extracts to prevent and treat acute and chronic cardiac and vascular complications and their sequelae, to prevent and treat thrombosis, to prevent and treat embolization in the setting of thrombosis, various arrhythmias and cardiac abnormalities, as well as to resolve hematomas

DETAILED DESCRIPTION OF THE INVENTION

Onion juice shall be extracted from plants not exposed to any heat beyond 80Celsius (preferably, plants shall be maintained at room temperature or below at all times). The ideal embodiment is extraction of onion juice from fresh onion bulbs that have not been frozen and are sterilized through other than chemical or caloric means.

Onion juice is expressed through mechanical means. Complete crushing of onions is recommended, as there may be some compounds inherent to cellular membranes that are of use. This juice is filtered to a standard depending on the projected mode of administration (parenteral formulations would have to adhere to accepted standards and regulations).

The juice may be further extracted with alcohol or other polar solvents (it is known that maximum activity is delivered by the water soluble component of onions, not the volatile oils which provide the predominance of the odor). This is not a necessary step, however, except to increase palatability for oral delivery).

This onion juice may be deposited onto charcoal or other adsorptive substrate directly (as described in GB235883), or may be desiccated by some other means. The avoidance or minimization of exposure to oxygen is suggested (such as the active pumping of nitrogen into the processing environment).

The use of whole desiccated or adsorbed onion juice is envisioned. Any subfractionated components of said juice are also possible. The optimal route of delivery is envisioned to be transdermal delivery. Whole desiccated onion juice would be integrated into a suitable transdermal delivery vehicle, with or without controlled release. In the case of onion juice it is known that even without any enhancement the active moieties of the juice will penetrate the skin rapidly and completely, resulting in effect identical to oral ingestion in most regards.

In the case of thrombolysis, whether for intravascular pathologies or an external hematoma, transdermal delivery is recommended due to its enhanced effect and rapidity of onset of action, due to its lack of gastrointestinal irritating potential, due to its reduced cost and due to its lowered allergenic or other side effect profile as compared to parenteral.

As with lidocaine, epinephrine, atropine and naloxone, liquid onion juice concentrate can be delivered via the pulmonary route.

Onion juice extract would be useful in the setting of prevention of cardiac and vascular pathologies related to hemostasis and its components. Such pathologies would include atherosclerosis, obstructive vascular disease and vascular disease in its initial stages that had not yet progressed to intraluminal disease. A wide variety of inflammatory conditions leading to vascular damage (such as rheumatoid disease and lupus erythematosus) would also benefit from chronic onion juice extract administration.

Onion juice extract affects the rheological properties of blood and would be useful in the setting of ischemia, peripheral, cardiac or cerebral. Onion juice would improve perfusion and reverse pathology in the setting of microvascular disease, such as Syndrome X and Burger's disease (endarteritis obliterans). Onion juice extract would also likely affect the progression of diseases that have so far not been firmly linked to endovascular pathology, such as Alzheimer's disease (or neurofibrillary plaque deposition).

Onion juice extract is useful in the setting of acute thrombosis, including—but not limited to—acute coronary events, cerebrovascular accident, stenotic vessel disease with or without acute main vessel thrombosis, deep vein thrombosis and pulmonary emboli.

As already noted, onion juice extract is an excellent potentiator of hematoma resorption. This would be useful in the case of trauma, as well as post-operative situations. It is of particular utility after cosmetic surgery.

Onion juice extract is expected to be combined with current standard of care in all clinical settings, if deemed advisable. The effect of onion juice extract is known to have approximately six hours in the body (other than in the case of controlled release formulations). Onion juice extract in quantities required to achieve the requisite clinical effects is not known to interfere with other medications and is not known to cause or increase the incidence of bleeding events.

Onion juice extract is expected to serve either as an adjunct, or replace Coumadin (Warfarin) in all settings where Coumadin is currently used (valvular disease, atrial fibrillation, other arrhythmias, ARVD—arrhythmogenic right ventricular tachycardia, other structural and essential cardiac arrhythmias and uncompacted myocardium). Coumadin is expensive, only partially effective and fraught with dangers. Onion juice does not cause excess bleeding and through its more expansive re-tuning of the entire hemostatic apparatus is expected to be at least equally effective to Coumadin. Further, there is also one report that attributes direct anti-arrhythmic effects to garlic (WO9405307). If this is true, it would be logical to assume that onions would also be likely to possess these properties, since onion juice is vastly more active in terms of its impact on the hemostatic mechanism than garlic. This antiarrhythmic property, however, is only conjecture at this point.

DISTINCTION FROM PRIOR ART

An exhaustive patent and literature search regarding garlic is provided.

A worldwide search revealed no patents regarding the medicinal properties and uses of onions. The only published articles found in world literature address the anti-platelet and anti-coagulant properties of onions in the vaguest of terms. They propose no practical applications, nor do they demonstrate an understanding of the implications of these properties.

Finally, one prior patent (GR1003636) observes that wild garlic extracts are sufficiently potent to warrant intravenous use for acute coronary syndromes. Onion extract is far more potent in this regard and, while also amenable to intravenous use due to its excellent biocompatibility, is readily absorbed through the skin and can be administered without any difficulty, or side effects, or requirements for intravenous equipment. Additionally, onion extract also possesses anticoagulant, antiplatelet and thrombolytic effects that garlic simply does not possess.

The invention claimed is:

1. A method of treating hematomas comprising the steps of:
   providing an extract of onion (*Allium cepa*); and
   topically applying the onion extract to or proximate an area of a hematoma, for transdermal delivery to increase and accelerate hematoma resorption.

2. A method as claimed in claim 1 wherein the step of topically applying is performed at multiple time intervals.

3. A method as claimed in claim 2 wherein the time intervals are approximately 6 hours.

4. A method as claimed in claim 1 wherein the extract is prepared at temperatures no greater than 80 degrees Celsius.

5. A method as claimed in claim 4 wherein the extract is prepared by a method comprising mechanically crushing an onion bulb produce onion juice.

6. A method as claimed in claim 5 wherein the extract is prepared by a method comprising obtaining water soluble components from the onion juice by filtering the onion juice and removing the water soluble components from volatile oils.

7. A method of treating thrombosis or cardiac arrhythmias in a subject in need thereof comprising the step of providing an extract of onion (*Allium cepa*), and transdermally administering the onion extract to a subject.

8. A method according to claim 7, wherein the step of transdermally administering is performed at multiple time intervals.

9. A method according to claim 8, wherein the extract is prepared at temperatures no greater than 80 degrees Celsius.

10. A method according to claim 9, wherein the extract is prepared by a method comprising mechanically crushing an onion bulb to produce onion juice.

11. A method according to claim 10, wherein the extract is prepared by a method comprising obtaining water soluble components from the onion juice by filtering the onion juice and removing the water soluble components from volatile oils.

* * * * *